| United States Patent [19] | [11] Patent Number: 4,950,602 |
| Cooper | [45] Date of Patent: Aug. 21, 1990 |

[54] INHIBITION OF LACTATE PRODUCTION BY PYRUVATE ADDUCTS

[75] Inventor: Arthur J. L. Cooper, Croton-on-Hudson, N.Y.

[73] Assignee: Cornell Research Foundation, Inc., Ithaca, N.Y.

[21] Appl. No.: 16,894

[22] Filed: Feb. 20, 1987

[51] Int. Cl.$^5$ .................. C12N 9/99; C07D 471/02
[52] U.S. Cl. .................. 435/184; 435/190; 536/27; 546/123; 546/215; 546/225; 546/237; 546/239
[58] Field of Search .................. 536/27; 546/123, 215, 546/225, 237, 239; 435/184, 190

[56] References Cited

PUBLICATIONS

Lappi et al., *Biochemistry*, 19: 3841–3845 (1980).
Kaplan et al., J. Biol. Chem., 221: 823–844 (1956).
Anderson et al., *J. Biol. Chem.*, 234: 1219–1232 (1959).
Anderson, "Analogs of Pyridine Nucleotide Coenzymes", in The Pyridine Nucleotide Coenzymes: Academic Press, Inc., N.Y. 1982 pp. 91–131.
Burgner et al., *Biochemistry*, 17: 1654–1661 (1978).
Everse et al., *Organic Chemistry*, 1: 207–233 (1971).
Burgner, *Biochemistry*, 23: 3636–3648 (1984).
Cooper et al., *J. Neurochem.*, 48: 1925–1933 (1987).

*Primary Examiner*—Robert A. Wax
*Attorney, Agent, or Firm*—Jones, Tullar & Cooper

[57] ABSTRACT

The present invention relates to inhibitors of lactate dehydrogenase that can cross the blood brain barrier and there is described herein the preparation of several analogues of nicotinamide-adenine-dinucleotide (NAD$^+$) pyruvate adduct, of which 3(-4-(reduced 3-pyridine aldehyde-adenine dinucleotide))-pyruvate (RAP) and similar compounds appear to have a very high affinity for lactate dehydrogenase; one of which (RAP) was shown to strongly inhibit lactate production in rat brain extracts.

11 Claims, 2 Drawing Sheets

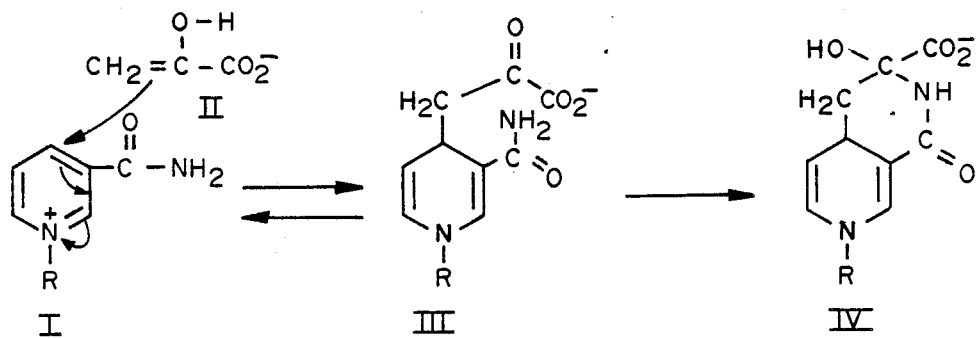
FIG. IA
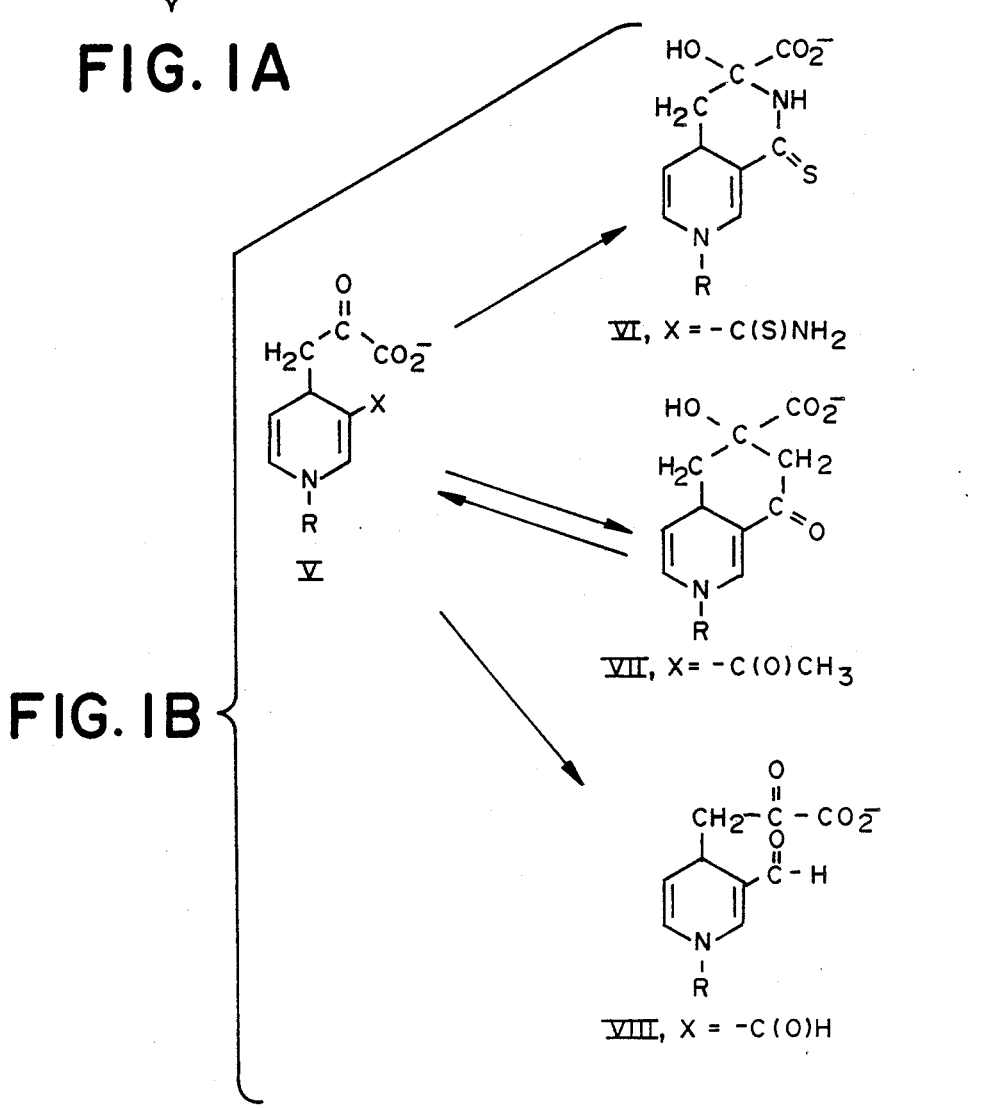
FIG. IB

INHIBITION OF LACTATE PRODUCTION BY PYRUVATE ADDUCTS

This invention was made at least in part under NIH Grant NS-03346. The U.S. Government has certain rights in this invention.

BACKGROUND OF THE INVENTION

Primary systemic lactic acidosis represents a serious and often fatal disorder of several possible causes. During ischemia brain lactate levels rise precipitously (Siesjo, 1978, "Brain Energy Metabolism," John Wiley and Sons; 1981, *J. Cereb. Flow Metab.*, 1:155–185; and references quoted therein). As discussed previously (Pulsineli, et al, 1982, *Neurology*, 32:1239–1246), brain lactate concentration is a function of several factors, including tissue oxygen tension (Gurdjian et al, 1944, *Arch. Neurol. Psychiatry*, 57:472–477), the glycolytic substrate supply from blood and brain (Ljunggren et al, 1974, *Brain Res.*, 77:173–186; Siesjo, 1981, supra) and the rate of lactate efflux into the venous circulation (Zimmer and Lang, 1975, *Am. J. Physiol.*, 229:432–437). Ljunggren et al, 1974, (supra) showed that, in the severely ischemic brain where the blood glucose oxygen supply approached zero and egress of lactate from brain is negligible, the tissue lactate concentration is proportional to cerebral stores of glycolytic substrate at the onset of the ischemic insult. In the four-vessel occlusion (4-VO) model of near-complete forebrain ischemia in the rat, lactate levels rise from a normal of $\sim 1.0$ mM to as high as 13.0 mM in normoglycemic animals (Pulsinelli et al, 1983, *J. Neurochem.*, 40:1500–1503; Kraig et al, 1985a, *Brain Res.*, 342:281–290). Forebrain ischemia under normoglycemic conditions results in selective neuronal destruction with the sparing of other tissue elements (Pulsinelli et al, 1983, supra). In contrast, equivalent degrees and duration of ischemia delivered during hyperglycemia produce tissue infarction with necrosis of all cellular elements. In this 4-VO model, lactate levels rise to greater than 16 mM in the hyperglycemic animals (Pulsinelli et al, 1982, supra) and may reach as high as 31 mM in total brain ischemia induced by cardiac arrest (Kraig et al 1985a, supra). It has been proposed that lactic acidosis, and the attendant decrease in pH, may be a major cause of severe ischemic brain injury (Myers, 1979, *Adv. Neurol.*, Vol. 26, Fahn et al, eds. pp. 195–213, Raven Press, N.Y.).

The relationship between brain lactate concentration and pH is complex and there is evidence of compartmentation of $H^+$ and of the principal buffer, bicarbonate (Kraig et al, 1985a, supra; 1985b, *Progress in Brain Res.*, Vol. 63, Kogure et al, eds. pp. 155–166: 1986, *Am. J. Physiol.*, 250:R348-R357). Nevertheless, in cardiac arrest, the brain pH of normoglycemic rats drops from $7.2\pm0.02$ to $6.79\pm0.02$ (brain lactate=8–12 mM) whereas the brain pH of hyperglycemic rats drops to $6.19\pm0.02$. Furthermore, in the 4-VO model of forebrain ischemia, the brain pH falls to 6.0–6.2 during the 30-minute insult and abruptly falls still further on reperfusion, to a low of 5.4 if the rat is severely hyperglycemic (Kraig et al, 1985b, supra). It is possible that the continued production of lactate in the brains of ischemic hyperglycemic animals occurred mostly in the astrocytes with a theoretical pH drop in these cells to as low as 5.2 or lower (Kraig et al, 1986, supra). Finally, Nordstrom et al, (1978a, *Stroke*, 9:327–335: 1978b, *Stroke*, 9:335–343, and 1978c, *J. Neurochem.*, 30:479–486) showed that incomplete cerebral ischemia (i.e. that accompanied by a small trickle of arterial blood) caused a rise of brain lactate that was twice that resulting from complete ischemia. The finding may explain in part the well-known observation that partial ischemia may be equally or more damaging to brain than similar durations of total ischemia (see also Kalimo et al, 1981, *J. Cerebral Blood Flow Metab.*, 1:313–327; Rehncrona et al, 1981, *J. Cerebral Blood Flow Metab.*, 1:297–311).

The weight of evidence favors lactic acidosis as a contributing factor to ischemic brain damage in normoglycemic animals; in hyperglycemic animals lactic acidosis may be the major contributing factor in converting selective neuronal damage into infarction during or following ischemia. The mechanism is unknown, but may be due in part to pH-induced changes in rates of reactions catalyzed by enzymes with narrow pH-activity profiles. Alternatively, Pulsinelli et al, (1985, *Cerebrovascular Diseases*, Plum and Pulsinelli, eds. pp. 201–210, Raven Press, N.Y.) have proposed that the lowered pH of ischemic brain favors the release and conversion of protein-bound $Fe^{3+}$ to free $Fe^{2+}$; the latter can then act as a source of highly reactive and damaging free radicals. Whatever the mechanism of the cell damage, a rational approach to minimizing ischemic damage to nervous tissue is to reduce lactic acid production as much as possible.

In addition to stroke, lactic acidosis is a serious complication in a number of general clinical settings in which (a) there is poor oxygen perfusion or (b) metabolism is disrupted by e.g. infections, hereditary causes, drug ingestion, liver damage, kidney damage or leukemia (for a discussion see Cohen and Woods, 1976, *Clinical and Biochem. Aspects of Lactic Acidosis*, Blackwell Sci. Pub., Oxford). Treatments have included sodium bicarbonate, trihydroxymethylaminomethane, electron acceptors (methylene blue), and glucose (with or without insulin): hemodialysis, peritoneal dialysis and $O_2$ have been used as therapeutic adjuncts (Cohen et al, supra). More recently, dichloroacetate has been employed in the treatment of animals with experimentally-induced lactic acidosis and of acidotic patients (e.g. Curry et al, 1985, *Clin. Pharmacol. Ther.*, 37:89–93 and references cited therein).

Apparently, dichloroacetate exerts its effect by activating pyruvate dehydrogenase (through inhibition of the kinase of the complex), thereby accelerating the removal of pyruvate before it can be reduced to lactate (for a review see Crabb et al, 1981, *Metabol.*, 30:1024–1039). However, dichloroacetate cannot prevent lactate buildup during ischemia because the conversion of pyruvate to acetyl CoA is an oxidative process. The best that dichloroacetate can accomplish is to hasten lactate removal following removal of the ischemic insult by which time tissue damage may have already occurred. Moreover, there is some evidence that dichloroacetate is neurotoxic, can cause cataracts and may be mutagenic. Finally, dichloroacetate interacts with many enzymes and is metabolized to toxic oxalate and highly reactive glyoxylate.

For the above reasons, it may be more advantageous to treat lactic acidosis (particularly that arising from an ischemic insult) with specific and reversible inhibitors of lactate dehydrogenase. The rationale is as follows. If lactate dehydrogenase is shut down, anaerobic glycolysis will halt because $NAD^+$ necessary for the glyceraldehyde-3-phosphate dehydrogenase reaction will not be regenerated. This in turn means that ATP will not be generated from phosphoglycerate and pyruvate kinases for the hexokinase and phosphofructokinase reactions. In the case of an ischemic insult, withdrawal of the insult should result in reestablishment of normal aerobic metabolism in that tissue. Aerobic glycolysis in non-ischemic tissue should not be greatly affected by inhibition of lactate dehydrogenase. There is a precedent for such reasoning: For example, Friede and VanHoutte (1961, *Exp. Neurol.*, 4:197–204) showed that cerebellar tissue slices undergo necrobiosis when cellular respiration is blocked selectively but not when respiration and glycolysis are blocked simultaneously. The problem then is the design of such a specific inhibitor of lactate dehydrogenase.

DESCRIPTION OF THE INVENTION

The present invention relates to inhibitors of lactate dehydrogenase that can cross the blood brain barrier and there is described herein the preparation of several analogues of nicotinamide-adenine-dinucleotide (NAD$^+$) pyruvate adduct, of which 3(-4-(reduced 3-pyridine aldehyde-adenine dinucleotide))-pyruvate (RAP) and similar compounds appear to have a very high affinity for lactate dehydrogenase: one of which (RAP) was shown to strongly inhibit lactate production in rat brain extracts.

In basic solutions, pyruvate enolizes and reacts (through its 3-carbon) with the 4-carbon of the nicotinamide ring of NAD$^+$ to yield an AND-pyruvate adduct in which the nicotinamide ring is in the reduced form. This adduct is a strong inhibitor of lactate dehydrogenase, presumably because it binds simultaneously to both pyruvate and NADH binding sites. The potency of the inhibition, however, is muted by the adduct's tendency to cyclize to a lactam (Everse et al, 1971, *Bioorgan. Chem.*, 1:207–233: Everse & Kaplan 1973, *Adv. Enzymol. Rel. Areas Mol. Biol.*, 37:61–133). Herein, solutions of the pyruvate adduct of NAD$^+$ and of NAD$^+$ analogues in which the —C(O)NH$_2$ of NAD$^+$ was replaced with —C(S)NH$_2$, —C(O)CH$_3$ and —C(O)H were prepared and characterized. Of the four, only the last analogue (RAP) cannot cyclize and it was found to be the most potent inhibitor of beef heart and rat brain lactate dehydrogenases. The IC$_{50}$ in the presence of either 0.2 or 2 mM pyruvate and 0.1 mM NADH is approximately 100 nM. Even at high concentrations RAP (20 $\mu$M) had little or no effect on rat brain glyceraldehyde-3-phosphate, pyruvate, $\alpha$-ketoglutarate, isocitrate, soluble and mitochondrial malate, and glutamate dehydrogenases. The glycolytic enzymes, hexokinase and phosphofructokinase were similarly unaffected. RAP strongly inhibited lactate production from glucose in rat brain extracts, but was less effective in inhibiting lactate production from glucose in synaptosomes. Rats injected intravenously with RAP (20 $\mu$moles/kg) exhibited no noticeable untoward effects and grew normally thereafter for at least 3 weeks. RAP, and similar non-cyclizing compounds, clearly are strong inhibitors of lactate dehydrogenase in vitro. Modification of RAP or related compounds (see below) may result in compounds that are useful for the reduction of lactic acidosis associated with human disease.

The compounds of the present invention correspond to the formulas:

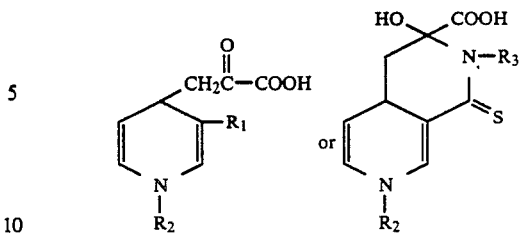

R$_1$ is halogen, —CN,

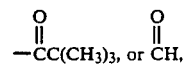

—CC(CH$_3$)$_3$, or CH,

R$_3$ is hydrogen or lower alkyl and where R$_2$ is

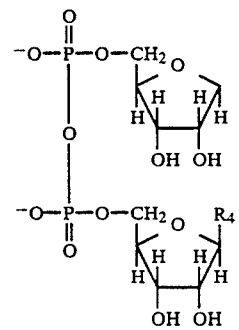

where x is 2 to 12 and where R$_4$ is

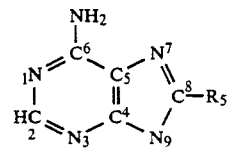

where R$_5$ is hydrogen, lower alkyl, for example having 1 to 8 carbon atoms, halogen or —N(CH$_3$)$_2$.

The compounds of the invention would be employed as in vitro inhibitors of lactate production. In addition the compounds of the invention would be administered to mammals (orally or intravenously) in amounts that are expected to inhibit lactate dehydrogenase in vivo, for example between about 0.1 and about 10 $\mu$mol/kg based upon theoretical considerations of the strength of binding of the inhibitors to lactate dehydrogenase to reduce lactic acidosis associated with human disease.

BRIEF DESCRIPTION OF THE DRAWINGS

FIG. 1 is a structural depiction of the reactions of the Examples. 1A. Addition of the 3-carbon of pyruvate enol (II) to the 4-carbon of the nicotinamide ring of NAD$^+$(I) (R=ribose-P$_i$-P$_i$-ribose-adenine). The resulting NAD-pyruvate adduct (III) cyclizes to a lactam structure (IV). 1B. Pyruvate adduct of NAD$^+$ analogs (V). When X=—C(S)NH$_2$ the adduct cyclizes to a lactam (VI) analogous to (IV). When X=—C(O)CH$_3$ reversible internal aldol condensation apparently occurs. Only in VIII (RAP) is cyclization theoretically impossible. Note that pyruvate enol can presumably add to both sides of the planar ring at the 4-position resulting in either an A or B hydrogen at the 4 position of structure V. Based on the findings of Burgner and Ray (*Biochemistry*, 23:3636–3648, 1984) it seems likely that the mixture contains approximately equal amounts of both isomers and A is the inhibitor.

EXAMPLES

Figure 2:
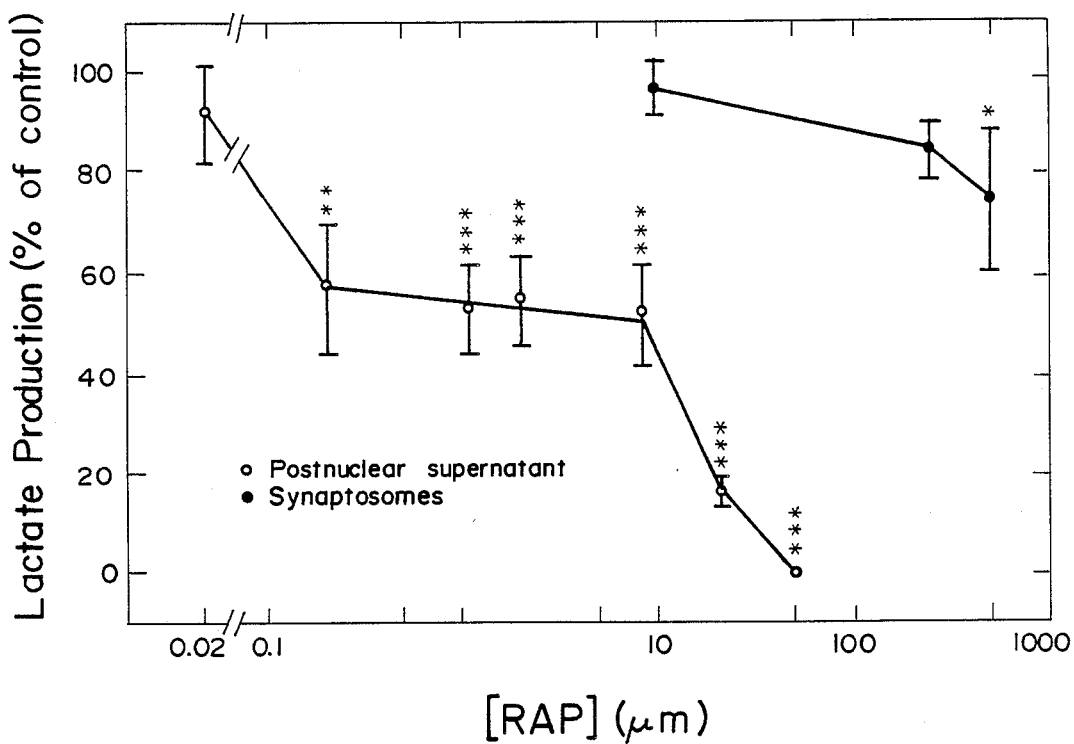
FIG. 2 is a graphic presentation of inhibition of lactate production from D-glucose by rat brain postnuclear supernatant fraction and by synaptosoms incubated with RAP. Lactate production was determined for a 20-min incubation at 37° C. Values (expressed as % of the control rate) are mean±SD of 3–6 determinations. The control value was 8.1±0.9 nmol of lactate produced/min/mg protein, *$P<0.05$, $P<0.03$ and *$P<0.005$ vs. control values.

Enzymes and enzyme assays. Rabbit muscle glyceraldehyde-3-phosphate dehydrogenase (80 U/mg: ammonium sulfate suspension), rabbit muscle glycerol-3-phosphate dehydrogenase (40 U/mg; ammonium sulfate suspension), beef liver glutamate dehydrogenase (120 U/mg: in 50% glycerol), mitochondrial pig heart malate dehydrogenase (1100 U/mg; in 50% glycerol) and yeast hexokinase (140 U/mg; ammonium sulfate suspension) were purchased from Boehringer Mannheim Corp. (Indianapolis). Beef heart lactate dehydrogenase (280 U/mg) was purchased from Worthington Biochemical Corporation (Freehold, N.J.). Porcine heart L-alanine aminotransferase (130 U/mg), rabbit muscle phosphofructokinase (140 U/mg; ammonium sulfate suspension), bovine heart α-ketoglutarate (8 U/mg) and pyruvate (5 U/mg) dehydrogenase complexes, sodium pyruvate, L-methionine-SR-sulfoximine, DL-vinylglycine, $NAD^+$, NADH and $NAD^+$analogues (3-acetylpyridine, thionicotinamide, and 3-pyridinealdehyde adenine dinucleotides) were purchased from Sigma Chemical Company (St. Louis, Mo.).

Each of the enzymes was assayed by procedures in which change of absorbance at 340 nm due to NADH was followed essentially as described by Bergmeyer (1974, *Methods of Enzymatic Analysis*, 2nd Eng. Ed., Verlag Chemie Weinheim Academic Press, N.Y.) with the following exceptions. Phosphofructokinase was assayed according to the method of Lai et al (1984, *J. Neurochem.*, 42:438–446). $NAD^+$-linked isocitrate dehydrogenase was assayed as described by Lai and Clark (1976, *Biochem. J.*, 154:423–432). Pyruvate and α-ketoglutarate dehydrogenase complexes were respectively assayed according to the methods of Lai and Sheu (1985, *J. Neurochem.*, 45:1861–1868) and Lai and Cooper (1986) (*J. Neurochem*, 47:1376–1386).

Preparation of rat brain extracts and synaptosomes

Postnuclear supernatant fraction (containing the glycolytic enzymes) was prepared from rat brain according to the method of Lai et al (1984, supra). Rat brain synaptosomes were prepared according to the method of Lai et al (1980, *Biochem. Pharmacol.*, 29:141–146). Lactate generated by these preparations in the presence of D-glucose was measured with lactate dehydrogenase as described by Lai et al (1984, supra), except that the concentrations of sodium phosphate buffer and nicotinamide used in the medium were respectively 5 and 20 mM. (In some cases where there was a carry over of appreciable RAP to the assay mix, ten times the recommended amount of lactate dehydrogenase was used and the effectiveness of the enzyme in converting lactate to pyruvate was checked by addition of lactate standards to the cuvette after the initial reaction was over).

Preparation of β,γ-unsaturated α-keto and α-hydroxy acids

Sodium arylidene pyruvates were prepared according to the method of Stecher et al, (1973, *J. Org. Chem.*, 38:4453–4457) except that NaOH was used in place of KOH. The 2,4-dinitrophenylhydrazone was precipitated from 0.1% 2,4 dinitrophenylhydrazine in 2 M HCl. The precipitate was dissolved in a minimum quantity of ethanol and reprecipitated with water. *Sodium furfurylidenepyruvate;* yield=67% Anal. calcd. for $C_8H_5O_4Na$: C 51.08, H 2.68. Found: C 51.23, H 2.81. *2,4-Dinitrophenylhydrazone.* Anal. calcd. for $C_{14}H_{10}N_4O_7$: C 48.56, H 2.91, N 16.18. Found: C 48.15, H 3.02, N 15.93, m.p., 196° C. *Sodium 4-(2-thienyl)-2-oxo-3-butenoate:* yield=75%. Anal. calcd. for $C_8H_5O_3SNa$: C 47.06, H 2.47. Found: C 46.83, H 2.58. 2,4-Dinitrophenylhydrazone. Anal. calcd. for $C_{14}H_{10}N_4O_6S\cdot H_2O$:C 44.21, H 3.18, N 14.73. Found: C 44.58, H 2.98, N 14.50. m.p. 183° C. *Sodium 4-(3-thienyl)-2-oxo-3-butenoate:* yield=40%. Anal. calcd. for $C_8H_5O_3SNa$: C 47.06, H 2.47. Found: C 46.45, H 2.57. *2,4-Dinitrophenylhydrazone.* Anal. calcd. for $C_{14}H_{10}N_4O_6S$:C 46.41, H 2.78, N 15.46. Found C 45.77, H 2.79, N 15.20. m.p. 208° C.

The parent compound, vinylglyoxylate ($CH_2$=$CHCOCO_2$, 2-oxo-3-butenoate) has apparently not been isolated either as the free acid or as a salt. Solutions were prepared by oxidizing L-methionine-SR-sulfoximine with L-amino acid oxidase in the presence of catalase (Cooper et al, 1976, *J. Biol. Chem.*, 251:6674–6682). (Due to the extreme reactivity the yield of vinylglyoxylate in solution was never more than 30% of the theoretical product as judged by ratio of carbonyl function to ammonia produced). Solutions of the next higher homologue, i.e. 2-oxo-3-pentenoic acid were similarly prepared by oxidative fragmentation of DL-α-methyl-DL-methionine-SR-sulfoximine.

Vinylglycolate was prepared from the corresponding cyanohydrin (Evans et al, 1973, *J.C.S. Chem. Comm.*, 55–56) by hydrolysis and precipitation of the zinc salt (Glattfield and Hoen, 1935, *J. Am. Chem. Soc.*, 57:1405–1407).

Preparation of solutions of NAD-pyruvate adduct and analogues

The procedure used was a modification of that of Everse et al (1971, supra) for the synthesis of the NAD-pyruvate adduct Sodium pyruvate (15 mg) and $NAD^+$(or $NAD^+$analogue) (100 mg) were dissolved in deaerated water. The pH was brought to 11.0 with concentrated NaOH. After standing at room temperature for one hour, the solution was applied to the top of a column of Whatman DE-52 (2×3 cm), washed with deaerated distilled water. The column was eluted with 30 ml of 25 mM ammonium bicarbonate at 4° C. Unreacted pyruvate, $NAD^+$and $NAD^+$analogues were eluted in this fraction. The highly-colored (yellow-orange) adducts were eluted with 5–6 ml of 25 mM ammonium bicarbonate containing 4% NaCl. The fraction was split into approximately 1 ml portions, flushed with nitrogen, and stored at −70° C. The NAD-pyruvate adduct is relatively unstable and easily oxidized with loss of absorbance at 340 nm (Everse et al, 1971, supra). Nevertheless, under the slightly alkaline conditions of storage and low temperature, these adducts remained stable for at least 3 months as judged by their continued potency toward inhibition of lactate dehydrogenase and maintenance of absorbance at 340 nm. The potency, however, was slowly lost on repeated freeze-thawing. The molar extinction coefficient of the NAD-pyruvate adduct at 340 nm is $8.1 \times 10^3$ (Everse et al, 1971, supra). The extinction coefficients at 340 nm of the three other adducts were assumed to be similar. The presence of a reactive carbonyl function was monitored as follows: 0.2–0.3 μ mole of the adduct was added to 50 μl of 0.1% 2,4-dinitrophenylhdrazine in 2 M HCl. After 10 minutes at room temperature, 0.8 ml of 1 M KOH was added. The absorbance at 430 nm was compared to equivalent amounts of pyruvate and $NAD^+$analogue taken through the same procedure.

Consistent with the preponderance of the lactam (FIG. 1, IV) the NAD-pyruvate adduct did not form a hydrazone (see also Everse et al, 1971, supra). The thionicotinamide compound (FIG. 1. V,X=—$C(S)NH_2$) similarly did not form a hydrazone and was also presumably cyclized (structure VI). The 3-acetylpyidine-compound (V, X=—$C(O)CH_3$) gave 1.5 reactive carbonyl equivalents, less than the predicted 2 carbonyls, and it is suspected that some cyclization (via internal aldol condensation) may have occurred (structure VII). This conclusion is also supported by the finding that the aldhyde analogue, which cannot possibly cyclize, is a stronger inhibitor than the acetylpyridine dinucleotidepyruvate adduct and by the rapid loss of inhibitory potency noted by Coulson et al, (1969, FEBS Lett., 3:333–337). In their review article, Everse et al (1973, supra) state that the acetylpyridine dinucleotide APAD-pyruvate adduct was prepared in their laboratory which unlike the $NAD^+$pyruvate analogue did not cyclize. However, no details were provided. Burgner and Ray (Biochemistry, 23:3636–3648 (1984)) have prepared solutions of APAD-pyruvate adduct. These authors find that the compound is relatively stable at pH 11.0 but reverts to free pyruvate and APAD at pH 7.0. RAP also has a tendency to revert to free pyruvate at neutral pH values ($t_{\frac{1}{2}}=90$ min). As expected, since no cyclization can occur with the 3-pyridine aldehyde compound (V, X=—$C(O)H$), two reactive carbonyl equivalents were found (structure VIII).

Animals. Brain tissue was obtained from young adult male Wistar rats (45–50 days old). In one series of experiments, rats that had previously been fed ad libitum were anesthetized with 4% halothane and a V-3 cannula was inserted in the femoral vein. The animals were immobilized by taping them to a lead brick. After they had recovered sufficiently, they were injected with the RAP solution. After initial observation for any side-reactions, the rats were untaped and their wounds were closed under anesthesia. The rats were then placed back in their cages for further observation.

Statistical Analysis. Significance was determined by the Mann-Whitney U test or by the Newman-Keuls test for multiple comparisons (Zhar, 1984, Biostatistical Analysis, 2nd Ed. Prentice Hall, Englewood, N.J.).

Interactions of NAD-pyruvate adduct and analogues with beef heart and rat brain lactate dehydrogenases The aldehyde analogue of the NAD-pyruvate adduct (i.e. RAP) is ~1000-fold more potent as an inhibitor of lactate dehydrogenase than is the NAD-pyruvate adduct itself (Table 1). Lowry and Passonneau (A Flexible System of Enzymatic Analysis, Academic Press, N.Y. 1972 p. 215) report a $K_m$ for NADH of 2.5 μM. From this value and using the standard equation for a competitive inhibitor one can calculate a $K_i$ for NAD-pyruvate adduct of 2.6 μM from the data in Table 1. The concentration of RAP required to inhibit the standard reaction by 50% is ~100 nM. Using the same analytical procedure one can calculate from the data in Table 1 that the $K_i$ for RAP is 2.6 nM (or 1.3 nM for the A form). Burgner and Ray (1984 supra) report a $K_i$ of 0.1 nM for inhibition of lactate dehydrogenase by APAD-pyruvate adduct. However this was for the dogfish enzyme. Higher values were obtained in the present work for the beef heart enzyme and for the enzyme in rat brain homogenates. In the present work the $K_i$ for APAD-pyruvate was estimated to be between 2 and 6 nM. The very low binding constant of RAP is in accord with the notion that it binds simultaneously to the pyruvate and NADH binding sites.

TABLE 1

Inhibition of beef heart and rat brain lactate dehydrogenases by NAD-pyruvate adduct and analogues

| Additive | Concentration | Relative Activity (%) Beef Heart | Relative Activity (%) Rat Brain |
|---|---|---|---|
| None (control) | — | [100] | [100] |
| NAD-pyruvate adduct | 34 μM | 90 | 48 |
|  | 68 μM | 62 | — |
|  | 136 μM | 38 | — |
| Thio analogue | 0.7 μM | 38 | — |
|  | 1.4 μM | 17 | 33 |
| Acetyl analogue | 0.08 μM | 90 | — |
|  | 0.42 μM | 60 | 61 |
|  | 0.84 μM | 21 | 30 |
| Aldehyde analogue[a] | 42 nM | 79 | 80 |
|  | 84 nM | 58 | 56 |
|  | 132 nM | 40 | 43 |
|  | 180 nM | 29 | 30 |

The reaction mixture (1 ml) contained 0.24 mM sodium pyruvate, 0.1 mM NADH, 100 mM potassium phosphate buffer (pH 7.2) and either purified bovine heart lactate dehydrogenase (0.01 U) or rat brain homogenate containing ~0.02 U of lactate dehydrogenase activity; 25° C. Since APAD-pyruvate adduct and RAP have a tendency to revert to pyruvate they were added to the reaction mixture just prior to addition of enzyme. Because the kinetics obtained with tight-binding inhibitors depends on the order of addition of substrates and inhibitors the enzyme was always added last. Each value is the average of at least 3 determinations. Each of the reaction rates in which an adduct was included in the reaction mixture was significantly different from the control with P < 0.05.
[a]Similar degrees of inhibition were obtained with 2.4 mM pyruvate at the fixed levels of RAP indicated. This finding suggests that RAP is a noncompetitive inhibitor with respect to pyruvate.

Interaction of RAP with other enzymes

At a concentration of 20 μM RAP in each reaction mixture did not inhibit the following enzymes in rat brain subcellular fractions: α-ketoglutarate, isocitrate and cytosolic malate dehydrogenases, and hexokinase nor did 20 μM RAP inhibit the purified bovine heart pyruvate dehydrogenase and α-ketoglutarate dehydrogenase complexes. Commercial and rat brain glutamate dehydrogenases and mitochondrial malate dehydrogenases were only slightly (equal to or less than 20%) inhibited. Everse et al (1971, supra), previously noted that a concentration of NAD-pyruvate adduct that inhibited chicken $H_4$ lactate dehydrogenase by 59% had little effect on pig heart mitochondrial malate, horse liver alcohol, yeast alcohol, and dogfish liver glutamate dehydrogenases.

Inhibition of lactate production from D-glucose in rat brain postnuclear supernatants and synaptosomes by RAP RAP inhibited lactate production from D-glucose in rat brain postnuclear supernatants in a concentration-dependent manner at concentrations higher than 200 nM (FIG. 2). Note that since RAP has a tendency to dissociate the true concentration present in solution is lower than that shown in the FIG. 2. The formal "concentration" required to inhibit lactate production by 50% is ~1-9 μM. At 2 μM initial concentration) it was shown that approximately 90% of the enzyme was tied up as the inactive E.RAP complex (the method for determining inactive enzyme complex was that of Burgner et al, (1978) *Biochemistry,* 17:1646–1653).

Much higher concentrations of RAP were required to inhibit lactate production in synaptosomes (FIG. 2) than in post-nuclear supernatants. At initial concentrations of 250–500 μM, RAP inhibited lactate production in synaptosomes by only 15–30% (FIG. 2). This apparent ineffectiveness can be explained by the diffusion barrier(s) to RAP posed by the synaptic plasma membranes. The compounds described herein are designed to overcome this problem, i.e., to cross biological membranes including the blood-brain barrier.

Effects of RAP in vivo

When RAP was administered intravenously to 4 rats (195-350 g) at a dose of 20 μmole/kg, no side effects were noted as judged by gross inspection of behavior. The animals survived for 3 weeks before being killed. Each rat grew and fed normally during this period. A gross post-mortem examination revealed no obvious tissue damage.

Rationale for the use NAD+analogue-pyruvate adducts

All attempts to synthesize reactive α-keto acids as inhibitors of lactate dehydrogenase failed. The arylidenepyruvates are ineffective. Vinylglyoxylate is an irreversible inhibitor of lactate dehydrogenase but is found to inhibit other enzymes, probably as a nonspecific alkylating agent. Vinylglycolate and 2-oxo-3-pentenoic acid are substrates, not inhibitors of the enzyme. The NAD+analogue-pyruvate adducts, therefore, seem to be the most promising. The adducts are selective and powerful inhibitors in vitro. However, to be active in vivo the compounds must be modified to improve stability and to cross biological membranes. Fortunately, a large number of modifications are theoretically possible. The present invention pertains to the design of NAD+pyruvate adducts that may be active in vivo.

I claim:

1. A compound corresponding to the formula

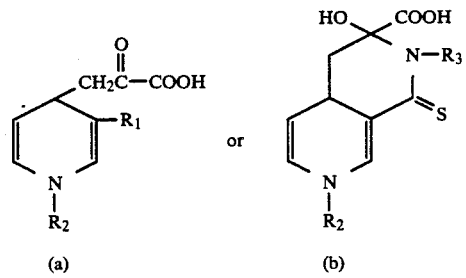

where $R_1$ is halogen, —CN,

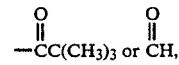

$R_3$ is hydrogen or lower alkyl and where $R_2$ is

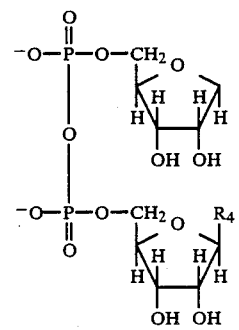

where x is 2 to 12 and where $R_4$ is

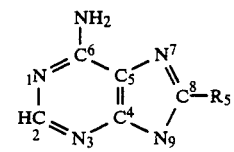

where $R_5$ is hydrogen, lower alkyl, halogen or —N(CH$_3$)$_2$.

2. Compound (a) as in claim 1 where $R_2$ is c).
3. The compound of claim 2 where $R_4$ is f).
4. The compound of claim 3 where $R_5$ is hydrogen.
5. The compound (b) as in claim 1 where $R_2$ is C).
6. The compound of claim 5 where $R_4$ is f).
7. The compound of claim 6 where $R_5$ is hydrogen.
8. Compound (a) as in claim 1 where $R_2$ is (d).
9. The compound of claim 8 where $R_4$ is (f).
10. The compound of claim 9 where $R_5$ is hydrogen.
11. A method of inhibiting lactate dehydrogenase by contacting the enzyme with an enzyme inhibiting amount of a compound as in claim 14.

* * * * *

UNITED STATES PATENT AND TRADEMARK OFFICE
CERTIFICATE OF CORRECTION

PATENT NO. : 4,950,602
DATED : August 21, 1990
INVENTOR(S) : Cooper

It is certified that error appears in the above-identified patent and that said Letters Patent is hereby corrected as shown below:

Column 3, line 31, delete "AND-" and insert in place thereof, --NAD- --.

Column 9, line 4, before "initial", insert --(--.

In the Claims:

Claim 1, line 35 of the column, delete "where x is 2 to 12".

Cancel claims 2, 3, 5, 6, 8 and 9.

Claim 11, change the reference from "Claim 14" to --Claim 1--.

Signed and Sealed this

Fifth Day of May, 1992

Attest:

DOUGLAS B. COMER

Attesting Officer

Acting Commissioner of Patents and Trademarks